(12) United States Patent
Paulista et al.

(10) Patent No.: US 7,479,279 B2
(45) Date of Patent: Jan. 20, 2009

(54) USE OF CYTOKINES OF THE TGF-β SUPERFAMILY FOR THE TREATMENT, INHIBITION AND/OR DIAGNOSIS OF SKIN RELATED DISORDERS

(75) Inventors: Michael Paulista, Leimen (DE); Jens Pohl, Hambrücken (DE)

(73) Assignee: Biopharm Gesellschaft zur biotechnologischen Entwicklung von Pharmaka, Heidelberg (DE)

( * ) Notice: Subject to any disclaimer, the term of this patent is extended or adjusted under 35 U.S.C. 154(b) by 123 days.

(21) Appl. No.: 10/472,389

(22) PCT Filed: Mar. 22, 2002

(86) PCT No.: PCT/EP02/03265

§ 371 (c)(1), (2), (4) Date: Sep. 23, 2003

(87) PCT Pub. No.: WO02/076494

PCT Pub. Date: Oct. 3, 2002

(65) Prior Publication Data

US 2004/0097456 A1    May 20, 2004

(30) Foreign Application Priority Data

Mar. 23, 2001  (EP) .................................. 01107265

(51) Int. Cl.
| | |
|---|---|
| A61K 39/00 | (2006.01) |
| A61K 8/18 | (2006.01) |
| C07K 1/00 | (2006.01) |
| C12P 21/02 | (2006.01) |
| C12N 1/20 | (2006.01) |
| C12N 15/00 | (2006.01) |

(52) U.S. Cl. ...................... 424/198.1; 512/12; 530/350; 435/69.5; 435/252.3; 435/320.1

(58) Field of Classification Search ........................ None
See application file for complete search history.

(56) References Cited

U.S. PATENT DOCUMENTS

| 5,194,596 | A | * | 3/1993 | Tischer et al. ............... 530/399 |
| 5,350,836 | A | * | 9/1994 | Kopchick et al. ........... 530/399 |
| 5,658,882 | A | * | 8/1997 | Celeste et al. ................. 514/12 |
| 6,027,919 | A | | 2/2000 | Celeste et al. |
| 6,120,760 | A | * | 9/2000 | Hotten et al. .............. 424/85.1 |
| 6,159,950 | A | | 12/2000 | Crystal et al. |
| 6,723,698 | B2 | * | 4/2004 | Rueger et al. ................. 514/12 |

FOREIGN PATENT DOCUMENTS

EP    1 074 620 A1    2/2001

OTHER PUBLICATIONS

Massague J. 1998. Ann. Rev Biochem. 67:753-91.*
Mikic B. 2004. Annals of Biomed. Engineering. 32:466-476.*
Kim et al. 1998. Pharmazie. 53:51-57.*
Yamashita et al. 1997. Exp. Cell Res. 235:218-226.*
Reddi AH. 2003. Chapter 51 in The Cytokine Handbook, ed by Thompson and Lotze, pp. 1179-1185.*
Vukicevic et al. 1996. PNAS USA 93:9021-9026.*
Pilbeam et al. 1993. Bone 14:717-720.*
Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 491-495.*
Singer et al. 1999. NEJM 341:738-746.*
Botchkareva N. V. et al., "New Roles for Glial Cell Line-derived Neurotrophic Factor and Neurturin: Involvement in Hair Cycle Control" American Journal of Pathology, 2000, vol. 156, No. 3, pp. 1041-1053, XP002211105.
Kim D. S. et al., "Effects of Growth Factors on the Proliferation of Human Keratinocytes and Fibroblasts in Vitro" Pharmazie, 1998, vol. 53, No. 1, pp. 51-57, XP001093948.
Wolfman et al., "Ectopic Induction of Tendon and Ligament in Rats by Growth and Differentiation Factors 5, 6 and 7, Members of the TGF-β Gene Family", J. Clin. Invest., vol. 100, No. 2, Jul. 1997, pp. 321-330.

* cited by examiner

*Primary Examiner*—Manjunath Rao
*Assistant Examiner*—Shulamith H Shafer
(74) *Attorney, Agent, or Firm*—Rothwell, Figg, Ernst & Manbeck, P.c.

(57) ABSTRACT

The present invention relates to the use of cytokines of the TGF-β-superfamily as well as nucleic acids encoding said cytokines for the treatment and diagnosis of skin related disorders, including hair and gland related disorders in mammals.

9 Claims, 5 Drawing Sheets

A

B

C

A

B

C

D

A

B

C

D

E

F

G

A

B

USE OF CYTOKINES OF THE TGF-β SUPERFAMILY FOR THE TREATMENT, INHIBITION AND/OR DIAGNOSIS OF SKIN RELATED DISORDERS

CROSS REFERENCE TO RELATED APPLICATION

This application is a 35 USC § 371 National Phase Entry Application from PCT/EP02/03265, filed Mar. 22, 2002, and designating the U.S.

The present invention relates to the use of cytokines of the TGF-β superfamily as well as nucleic acids encoding said cytokines for the treatment and diagnosis of skin related disorders including hair and gland related disorders, particularly hair loss, in mammals.

MP52 (also known as GDF-5) is a bone morphogenetic protein like molecule which belongs to the transforming growth factor beta (TGF-β) superfamily and is known to stimulate inter alia bone and cartilage formation. Similar to other members of this protein superfamily MP52 also influences neurotrophic functions (see, e.g., WO-A-93/16099, WO-A-95/04819, WO-A-97/03188 and WO-A-99/15191 for a description of the various functions and effects of MP52). For example, TGFβ-1, -2, and -3, as well as activin A, bone morphogenetic proteins (BMP)-2, -4, -6, -7, -12, glial cell line-derived neurotrophic-like factors (GDNF-like), and MP52 have all been shown to promote the survival of midbrain dopaminergic neurons by various mechanisms. GDNF also acts on a wide spectrum of peripheral neurons.

MP121 (also known as activin C) is an activin like molecule which belongs to the transforming growth factor beta (TGF-β superfamily (See WO-A-93/16099, WO-A96/01316 and WO 98/22492) and is known to influence for example liver growth and neurotrophic functions (see, e.g., WO-A-97/03188, WO-A-96/01316 and WO 98/22492).

TGF-βs are widely distributed and contextually acting cytokines with prominent roles in development and cell cycle control. TGF-βs were found to be useful in connection with the treatment of a wide variety of disorders, in particular such disorders being in conjunction with wound healing, neuronal survival and tissue repair.

Within the mammalian body the epidermal cell layers of the skin represent the largest organ. The skin consists of a mesenchymatic and an epithelial compartment. Furthermore, the epidermis creates hair follicles as well as several types of secretory glands. Due to the complex interrelations between the two compartments of the skin growth factors play an important role in biochemical signalling and therefore contribute to the preservation of both structure and function of the hairy skin. During the last years several cytokines, e.g. IL-1 and HGF, could be detected in skin cells.

Until now, the treatment of several skin related disorders, e.g. hair loss and other disorders of hair growth is only marginally feasible by pharmaceutical means. To date, the methods of most success concerning hair loss are surgical methods such as transplantation which represent inter alia complicated and expensive approaches which additionally are of high strain for the patient.

Thus, the technical problem underlying the present invention was to provide a possibility for the treatment, prevention and diagnosis of skin related disorders, e.g. hair loss and hair growth disorders, which avoids the drawbacks of the hitherto used methods.

This problem is solved by the present invention as specified in the claims.

In particular, the present invention relates to the use of a cytokine of the TGF-superfamily or a functionally active derivative or part thereof and/or a nucleic acid having a nucleotide sequence encoding said cytokine or a functionally active derivative or part thereof for the preparation of a composition for the treatment and/or prevention and/or diagnosis of skin, gland and hair related disorders, e.g. hair loss and growth disorders, gland related disorders in mammals, preferably humans.

The term "cytokine of the TGF-β superfamily" refers to a proteinaceous compound, in particular a protein or polypeptide comprising a conserved 7 cystein knot motif characteristic for the members of this cytokine family. The terms "functionally active derivative" and "functionally active part" refer to a proteinaceous compound exhibiting at least part of the biological function of the respective cytokine and comprise also biosynthetic mutants or derivatives. Such useful "derivatives" or "parts" can easily be detected by the man skilled in the art. For the derivatives such molecules are especially considered to be comprised by the above definition, wherein conservative amino acid substitutions occur. Such conservative amino acid substitutions mostly do not affect the biological functions of the proteins. Generic sequences comprising the seven cystein regions correspond to the following formula:

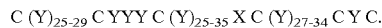

$$C\ (Y)_{25-29}\ C\ YYY\ C\ (Y)_{25-35}\ X\ C\ (Y)_{27-34}\ C\ Y\ C.$$

In this formula, C denotes cysteine and Y as well as X denote any amino acid including cysteine. In case where dimeric proteins are desirable X is a cysteine. In cases where monomeric proteins are desirable X is any amino acid except cysteine. Proteins or polypeptides which correspond to this generic sequences are generally applicable within the context of the present invention. It is also especially preferred that derivatives containing the seven or six cysteine region show at least 70% and preferably 80% homology to that of the naturally occurring protein form. It is also preferred that concerning variants all the cysteine residues of the seven cysteine region are conserved at their respective position in the naturally occurring protein, i.e. with the already known distance from each other. Especially on the N-terminal part of mature morphogenetic proteins substitutions or deletions affect the biological activity to a lesser degree, if at all. It is therefore to be understood that proteins containing further deletions or substitutions in their N-terminal part are also considered as proteins which are useful for the present invention.

Interesting members of the TGF-β superfamily or active variants thereof comprise the TGF-β proteins like TGF-β1, TGF-β2, TGF-β3, TGF-β4 TGF-β5 (U.S. Pat. No. 5,284,763; EP0376785 U.S. Pat. No. 4,886,747; DNA 7 (1988) page 1-8), EMBO J. 7 (1988) page 3737-3743), Mol. Endo. 2 (1988) page 1186-1195), J. Biol. Chem. 265 (1990) page 1089-1093), OP1, OP2 and OP3 proteins (U.S. Pat. Nos. 5,011,691, 5,652,337, WO 91/05802) as well as BMP2, BMP3, BMP4 (WO 88/00205, U.S. Pat. No. 5,013,649 and WO 89/10409, Science 242 (1988) page 1528-1534), BMP5, BMP6 and BMP-7 (OP1) (Proc. Natl. Acad. Sci. 87, (1990) page 9841-9847, WO 90/11366), BMP8 (OP2) (WO 91/18098), BMP9 (WO 93/00432) BMP10 (WO 94/26893), BMP11 (WO 94/26892), BMP12 (WO 95/16035), BMP13 (WO 95/1 6035), BMP15 (WO 96/36710), BMP16 (WO 98/12322), BMP3b (Biochem. Biophys. Res. Comm. 219 (1996) page 656-662), GDF1 (WO 92/00382 and Proc. Natl. Acad. Sci. 88 (1991) page 4250-4254), GDF8 (WO 94/21681), GDF10 (WO 95/10539), GDF11 (WO 96/01845), GDF5 (CDMP1, MP52) (WO 95/04819; WO 96/01316; WO 94/15949, WO 96/14335 and WO 93/16099 and Nature 368

(1994) page 639-643), GDF6 (CDMP2, BMP13) (WO 95/01801, WO 96/14335 and WO 95/16035), GDF7 (CDMP3, BMP12) (WO 95/01802 and WO 95/10635), GDF14 (WO 97/36926), GDF15 (WO99/06445), GDF16 (WO99/06556), 60A (Proc. Natl. Acad. Sci. 88 (1991) page 9214-9218), DPP (Nature 325 (1987) page 81-84), Vgr-1 (Proc. Natl. Acad. Sci. 86 (1989) page 4554-4558) Vg-1, (Cell 51(1987) page 861-867), dorsalin (Cell 73(1993, page 687-702), MIS (Cell 45 (1986) page 685-698), pCL13 (WO 97/00958), BIP (WO 94/01557), inhibin a, activin βA and activin βB (EP 0222491), activin βC (MP121) (WO 96/01316), activin βE and GDF12 (WO96/02559 and WO98/22492), activin βD (Biochem. Biophys. Res. Comm. 210 (1995) page 581-588), GDNF (Science 260 (1993) page 1130-1132, WO 93/06116), Neurturin (Nature 384 (1996) page 467-470), Persephin (Neuron 20 (1998) page 245-253, WO 97/33911), Artemin (Neuron 21 (1998) page 1291-1302), Mic-1 (Proc. Natl. Acad. Sci USA 94 (1997) page 11514-11519), Univin (Dev. Biol. 166 (1994) page 149-158), ADMP (Development 121 (1995) page 4293-4301), Nodal (Nature 361 (1993) page 543-547), Screw (Genes Dev. 8 (1994) page 2588-2601). Other useful proteins include biologically active biosynthetic constructs including biosynthetic proteins designed using sequences from two or more known morphogenetic proteins. Examples of biosynthetic constructs are disclosed in U.S. Pat. No. 5,011,691 (e.g. COP-1, COP-3, COP-4, COP-5, COP-7 and COP16).

The disclosure of the cited publications including patents or patent applications are incorporated herein by reference.

Functional parts of these proteins as well as derivatives as defined above are also comprised for the present invention.

Other cytokines may be useful as for example NGF, neutrophins such as NT-3 or NT-4, EGF, EGF-like proteins, VEGF, TGF-a, CNTF, BDNF, FGF such as FGF-2, IGF or KGF. These cytokines may be especially useful in combination with cytokines of the TGF-β family.

EP 1 074 620 describes monomeric proteins of the TGF-β family. Such monomeric proteins can also be used according to the present invention as long as they show at least partially the biological properties of the respective dimeric proteins.

Further, nucleic acids encoding any of the above mentioned proteins as well as derivatives or functional parts thereof can be used within the context of the present invention. The nucleic acids encoding the proteins referred to above are known. However, also nucleic acids that differ from the known sequences due to the diversity of the genetic code but code for the same protein are also useful. The nucleic acids may be naturally occuring nucleic acids or recombinantly produced as well as processed nucleic acids. The nucleic acids can be DNA or RNA as long as a protein or protein derivative or part of any of these can be obtained using such nucleic acid. This embodiment relates to the surprising finding that a nucleic acid encoding a morphogenetic protein can express the protein also directly at the site of action and then the full efficacy of the protein is obtained.

A particularly preferred cytokine for the use in the present invention is MP52.

For MP52 several modifications are already described, especially proteins which are truncated on the N-terminus. The mature form of MP52 can start with Arg, Ala or Pro. Further deletions on the N-terminal part are without effect on the biological activity, as long as the region comprising the seven cysteines is present and this region retains at least 70% and preferably 80% homology to the natural sequence of MP52. Additions at the N-terminus can be advantageous e.g. for protein purification purposes.

Another particularly preferred cytokine for the use in the present invention is MP121.

For MP121 several modifications are already described, especially proteins which are truncated on the N-terminus of the mature protein (WO 96/01316). Further deletions on the N-terminal part are without effect on the biological activity, as long as the region comprising the seven cysteines is present and this region retains at least 70% and preferably 80% homology to the natural sequence of MP121. Additions at the N-terminus can be advantageous e.g. for protein purification purposes.

According to a further preferred embodiment of the present invention, the composition comprises at least one further cytokine of the TGF-β superfamily or a functionally active derivative or part thereof, for example one or more of the cytokines as defined above and/or one or more nucleic acid(s) encoding said cytokines or functionally active derivatives or parts thereof.

In another preferred embodiment the invention can be used to improve skin related disorders such as wound healing or wound repair.

Tissue regeneration appears to be controlled by specific peptide factors which regulate the migration and proliferation of cells involved in the repair process (Barrett, T. B. et al., Proc. Natl. Acad. Sci. USA 81:6772-6774 (1985); Collins, 1. et al., Nature 316:748-750 <1985)). Ihus, growth factors may be promising therapeutics in the treatment of wounds, burns and other skin disorders (Rifkin, D. B. and Moscatelli, J. Cell. Biol. 109:1-6 (1989); Sporn, M. B. et al., J Cell. Biol. 105: 1039-1045 (1987); Pierce, G. F. et al., J. Cell. Biochem. 45; 319326 (1991)).

Impaired wound healing may result in such complications as dehiscence, anastomotic breakdown and non-healing wounds. Impaired healing is often associated with diseases such as diabetes, infection, immunosuppression, obesity and malnutrition (Cruse, P. J. and Foord, R., Arch. Surg. 107:206 (1973); Schrock, 1. R. et al., Ann. Surg. 177:513 (1973); Poole, G. U., Jr., Surgery 97:631 (1985); Irvin, G. L. et al., Am. Surg. 51:418 (1985)). Three phases have been described in normal wound healing: acute inflammatory phase, extracellular matrix and collagen synthesis, and remodeling (Peacock, E. E., Jr., Wound Repair, 2nd edition, W B Saunders, Philadelphia (1984)). The process involves the interaction of keratinocytes, fibroblasts and inflammatory cells at the wound site.

The sequence of the healing process is initiated during an acute inflammatory phase with the deposition of provisional tissue. This is followed by re-epithelialization, collagen synthesis and deposition, fibroblast proliferation, and neovascularization, all of which ultimately define the remodeling phase (Clark, R. A. F., J. Am. Acad. Dermatol. 13:701 (1985)). These events are influenced by growth factors and cytokines secreted by inflammatory cells or by the cells localized at the edges of the wound (Assoian, R. K. et al., Nature (Lond) 309:804 (1984); Nemeth, G. G. et al., "Growth Factors and Their Role in Wound and Fracture Healing," Growth Factors and Other Aspects of Wound Healing in Biological and Clinical Implications, New York (1988), pp. 1-17.

Another embodiment of the further invention relates to an agonist as a substitute for the functional activity for the above mentioned cytokines.

In another preferred embodiment of the invention the skin related growth disorder is a hair growth disorder.

The hair cycle involves three distinct phases: anagen (active hair growing), catagen (transition stage, follicle activity declines), and telogen (resting, no cell proliferation can be measured).

The bulge stem cells are activated by dermal papillae during late telogen. This is termed "bulge activation". The dermal papillae are activated by the matrix during mid-anagen. Matrix cells are in fact, TA cells; therefore, matrix cells have a limited proliferative potential. The upward movement of dermal papillae is important for the activation of hair stem cells. Defects in any of these elements can result in abnormal hair growth or hair loss.

The preferred hair growth disorder which may be treated and/or prevented and/or diagnosed according to the present invention is hair loss (e.g. alopecia of the immediate type, Jonston's alopecia, male-pattern baldness and alopecia of the late type, Alopecia areata).

Furthermore, the hair growth disorders to be treated and/or prevented and/or diagnosed according to the invention are preferably caused by fungal infections such as Dermatophytosis or bacterial infections such as *Cryptococcosis* or *staphylococcal dermatitis* lesions.

Furthermore, the hair growth disorders to be treated and/or prevented and/or diagnosed according to the invention are preferably caused by thyroic gland disorders.

Furthermore, the hair growth disorders to be treated and/or prevented and/or diagnosed according to the invention are preferably caused by a pharmaceutical drug. Examples for medications that are known to cause hair loss are cancer chemotherapy medications, parkinson medications such as levodopa (Dopar, Larodopa), ulcer drugs such as cimetidine (Tagamet), ranitidine (Zantac) and famotidine (Pepcid), anticoagulents such as Coumarin and Heparin, agents for gout such as Allopurinol (Loporin, Zyloprim), antiarthritics such as penicillamine, auranofin (Ridaura), indomethacin (Indocin), naproxen (Naprosyn), sulindac (Clinoril), drugs derived from vitamin-A such as isotretinoin (Accutane) and etretinate (Tegison), anticonvulsants for epilepsy such as trimethadione (Tridione), antidepressants such as tricyclics and amphetamines, beta blocker drugs for high blood pressure such as atenolol (Tenormin), metoprolol (Lopressor), nadolol (Corgard), propranolol (Inderal) and timolol (Blocadren), antithyroid agents such as carbimazole, Iodine, thiocyanate, thiouracil, blood thinners, male hormones.

Furthermore, the present invention can also be used to prevent hair growth. One possible application is to protect the hair follicle cells from cell death caused by a cytotoxic agent during e.g. cancer therapy. Another possible application is the prolongation of depilation or the reduction of hair growth for aesthetic reasons.

Preferably, the composition as defined above and prepared for the treatment and/or prevention of hair growth disorders additionally contains a pharmaceutically acceptable carrier and/or diluent and may preferably be applied orally, topically, intravenously and/or parenterally. Thereby, the carrier and/or diluent which may be used in the pharmaceutical composition according to the present invention depends on the administration route which also influences the final formulation such as, for example, ointments, drops, gel formulations or solutions for injection.

The pharmaceutical composition which is prepared according to the present invention typically includes a pharmaceutically effective amount of the above-defined cytokine or a functionally active derivative and/or part thereof and/or the above-defined nucleic acid which encodes the cytokine in combination with one or more pharmaceutically and physiologically acceptable formulation materials such as a carrier and/or a diluent. Further formulation components include antioxidants, preservatives, colouring, flavouring and emulsifying agents, suspending agents, solvents, fillers, bulking agents, buffers, delivery vehicles, excipients and/or pharmaceutical adjuvants. For example, a suitable carrier or vehicle may be water for injection, physiological saline solution, or a saline solution mixed with a suitable carrier protein such as serum albumin. A preferred antioxidant for the preparation of the composition of the present invention is ascorbic acid.

The pharmaceutical preparations of the present invention can be used, as stated above, for the promotion or inhibition of hair growth, and as such, are to be considered cosmetic compositions. Cosmetic compositions known in the art, preferably hypoallergic and pH controlled are especially preferred, and include toilet waters, packs, lotions, skin milks or milky lotions. Said preparations contain, besides the active compound, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

The solvent or diluent of the pharmaceutical composition may be either aqueous or non-aqueous and may contain other pharmaceutically acceptable excipients which are capable of modifying and/or maintaining a pH, osmolarity, viscosity, clarity, scale, sterility, stability, rate of dissolution or odour of the formulation. Similarily other components may be included in the pharmaceutical composition according to the present invention in order to modify and/or maintain the rate of release of the pharmaceutically effective substance, such as the MP52 protein or to promote the absorption or penetration thereof across the epithelial and/or stromal cells. Such modifying components are substances usually employed in the art in order to formulate dosages for parenteral administration in either unit or multi-dose form.

The finally formulated pharmaceutical composition prepared according to the present invention may be stored in sterile vials in form of a solution, suspension, gel, emulsion, solid or dehydrated or lyophilized powder. These formulations may be stored either in a ready-to-use form or in a form, e.g. in case of a lyophilized powder, which. requires reconstitution prior to administration.

The above and further suitable pharmaceutical formulations are known in the art and are described in, for example, Gus Remington's Pharmaceutical Sciences (18th Ed., Mack Publishing Co., Eastern, Pa., 1990, 1435-1712). Such formulations may influence the physical state, stability, rate of in vivo release and rate of in vivo clearance of the pharmaceutically effective component, such as the TGF-β like protein and/or the nucleic acid as defined above. Other effective administration forms comprise parenteral slow-release, i.e. retarded, formulations, inhalent mists, or orally active formulations. For example, a slow-release formulation may comprise MP52 and/or another member of the TGF-β superfamily or a functionally active derivative or part thereof which may be bound to or incorporated into particulate preparations of polymeric compounds (such as polylactic acid, polyglycolic acid, etc.) or liposomes. According to a further preferred embodiment of the present invention hyaluronic acid may be used as a carrier for the pharmaceutically active component, e.g. MP52, which may have the effect of promoting sustained duration in the circulation. The pharmaceutical composition according to the present invention may also be formulated for parenteral administration, e.g., by infusion or injection, and may also include slow-release or sustained circulation formulations. Such parenterally administered therapeutic compositions are typically in the form of pyrogen-free, parenterally acceptable aqueous solutions comprising the pharmaceutically effective component(s) such as MP52 in a pharmaceutically acceptable carrier and/or diluent.

Especially preferred formulations for pharmaceutical compositions for treating hair growth disorders are polymeric gel formulations comprising a polymer which may be selected from the group consisting of vinyl polymers, polyoxy ethylene-polyoxy propylene copolymers, polysaccharides, proteins, poly(ethylene oxide), acrylamide polymers and derivatives or salts thereof. Such gel formulations are described in, e.g., U.S. Pat. No. 5,705,485.

Gel formulations comprising a water-soluble, pharmaceutically compatible polymeric material advantageously influence the viscosity of the pharmaceutical composition within various ranges determined by the application, since the formulations are capable of controlling the release and increased contact time of the pharmaceutically active component to the site of action. Especially preferred examples of gel formulations containing a polymeric material are hyaluronic acid gel formulations.

Hyaluronic acid (HA) is one of the mucopolysaccharides having a straight chain structure consisting of the repetition of a disaccharide unit of N-acetyl glucosamine and glucuronic acid. HA is found in nature, microorganisms and in the skin in connected tissue of humans and animals. Molecular weights of HA are within the range of from 50,000 to 8,000,000 depending on source, preparation and method of determination. Viscous solutions of HA have lubricating properties and an excellent moisturizing effect. It is found in the synovial fluid of joints, vitreous body of the eye ball, umbilical cord, skin, blood vessels and cartilage. HA works remarkably well as a lubricant and shock absorbing agent, and this is probably due to its water-retaining ability and its affinity for. linking of certain specific proteins. It is considered to be a very safe molecule for internal use especially within the human body. Thus, it may be used in the pharmaceutical composition according to the present invention for the treatment of hair growth disorders, such as hair loss. Furthermore, the excellent lubricating properties and moisturizing effects of HA are highly advantageous for a pharmaceutical composition according to the present invention which may be, e.g., used for the treatment of hair growth disorders. Preferably, hyaluronic acid is present in concentrations of 0.5 to 5.0% by weight, based on the total weight of the pharmaceutical composition. Such a concentration range is suitable for the formulation of light viscous solutions which may be used as a liquid having a viscosity which is preferably in the range of 1 to 1,000 mPas as well as for other forms of applications such as soaking bandages, wherein the viscosity is preferably in the range of 1.0 to 5,000 mPas.

According to a preferred embodiment of the pharmaceutical composition according to the present invention, the pharmaceutically effective component, such as MP52, preferably recombinant human MP52, may be present in concentrations ranging from 0.01 to 1 mg/ml, for example in the case of liquid formulations such as gel formulations or formulations based on water or ethanol.

Another skin related disorder that can be treated with the composition which is prepared according to the present invention is a gland disorder as e.g. a sweat gland disorder. The above disclosure for pharmaceutical compositions relating to skin related growth disorders in general and especially to hair growth disorders can equally be applied to patients with abnormal sweat gland activities. This treatment and/or prevention of other gland disorders is another preferred embodiment of the present invention.

Although the exact mechanism by which cytokines influence skin cells has not yet been determined in detail it seems as if cytokines and especially MP52 affect the production of hair fibers by acting on stem cell migration and/or on the differentiation and proliferation of stem cell progenitors in hair follicles. Furthermore, MP52 induces angiogenesis and is therefore capable of improving the blood supply for hair and skin related cells. The lowest part of the hair follicle is called bulb region. It is followed by the intermediate region and the bulge region. At the top of the hair follicle there is the sebaceous gland region. A hair is formed of terminally differentiated hair cells located in the bulb region.

Furthermore hair follicles consist of an epithelial core surrounded by a mesenchymal sheath, which is in continuity with the follicular papilla in the hair bulb. The epithelial core itself consists of layers called outer root sheath (ORS), inner root sheath (IRS), IRS cuticle, hair cuticle, cortex and medulla. Those layers are characterized by individual and specific programs of differentiation.

The upper bulge region of the follicle contains a population of multipotent stem cells and/or progenitor cells, which are able to generate all the epithelial lineages present in hairy skin, because they have the capacity to respond to morphogenetic signals such as growth factors. At the initiation of a new hair cycle (during hair formation) these stem cells migrate from the upper bulge region to the lower bulb region of the follicle and initiate hair growth. MP52 may affect the production of hair fibers by acting on stem cell migration and/or on the differentiation and/or proliferation of stem cell progenitors in hair follicles.

Cytokines may have adverse effects on hair follicles and other skin cells and glands. It is possible that in situtations which can be described as skin and especially hair growth or gland disorders too little cytokine is present or acting effectively in the cells. In such a situation it is useful to administer additional cytokine as is possible with the above described embodiment of the present invention. Cytokine, and especially MP52 is administered to the skin and the cytokine can substitute for lacking or ineffective cytokine in the cell.

In another situation, however, it is conceivable that an excess of cytokine may cause a disregulation within the cell. Possible mechanisms of cytokines effecting hairloss may be:

Cyctokines may affect regulation of steroid 5 alpha-reductase (enzyme which creates Dihydrotestosterone).

Cytokines may promote lyse of the collagen gel matrix in hair follicles.

Cytokines may enhance production of metalloproteinase stromelysin in papilla cells.

Cytokines may acts as a negative growth factor cytokines may upregulate collagen mRNAs.

Cytokines may inhibit keratinocyte proliferation.

Cytokines may induce keratinocyte apoptosis.

Cytokines may improve blood supply by widening of existing or creation of new blood vessels.

Cytokines may promote mitosis of hair related cells.

Cytokines may affect innervation of hair related cells.

Also other epidermal cell types may be effected by an excess of cytokines:

Suprabasal cells of the proliferating epidermis.

Suprabasal keratinocytes of the epidermis.

Cells of the hair bulb cortex in the hair follicles.

Precortex cells at the base of the hair shaft in mature hair follicles.

Hair follicle dermal papilla cells.

Dermal sheath cells.

Interstitial dermal fibroblasts.

Gland cells.
Nerve cells.
Endothelial (blood vessel) cells.
Cells of the Merkel or Langerhans type.

For all these situations it may be desirable to remove excess cytokine or to avoid the development of such excess.

To cope with this problem two possibilities are proposed within the context of the present invention.

The first possibility is concerned with the use of a cytokine antagonist and its administration for the treatment or prevention of skin related disorders including gland or hair related growth disorders in mammals.

A further subject of the present invention, therefore, is the use of a cytokine antagonist and preferably an MP52 antagonist for the preparation of a composition for the treatment and or prevention of skin related growth disorders in mammals, wherein preferably the skin related disorder is a hair growth disorder or gland, especially sweat gland disorder.

Cytokine antagonists are known in the art, for MP52 for example from WO 00/21998. These antagonists can be used instead of the cytokine itself within the context of the invention as described above.

The second possibility is concerned with antibodies against cytokines. Such antibodies can also inactivate cytokines present in cells. Therefore another subject of the present invention is the use of an antibody, preferably a monoclonal antibody against a cytokine, preferably MP52, for the preparation of a composition for the treatment and/or prevention of skin related growth disorders as described above. Antibodies against cytokines are well known in the art. A monoclonal antibody specific for MP52 is for example described in WO 97/43408. Also such antibodies can be used in compositions as they have been described above instead of a cytokine.

The compositions prepared according to the present invention may be used for cosmetic purposes as well.

For diagnostic purposes, for example the nucleic acid as defined above may be preferably used for the preparation of compositions suitable for use in RT-PCR, blotting techniques (Northern blot, Southern blot), DNA chip technology etc.

The patent or application file contains at least one drawing executed in color. Copies of this patent or patent application publication with color drawing(s) will be provided by the Office upon request and payment of the necessary fee.

EXAMPLES

Figure 1:
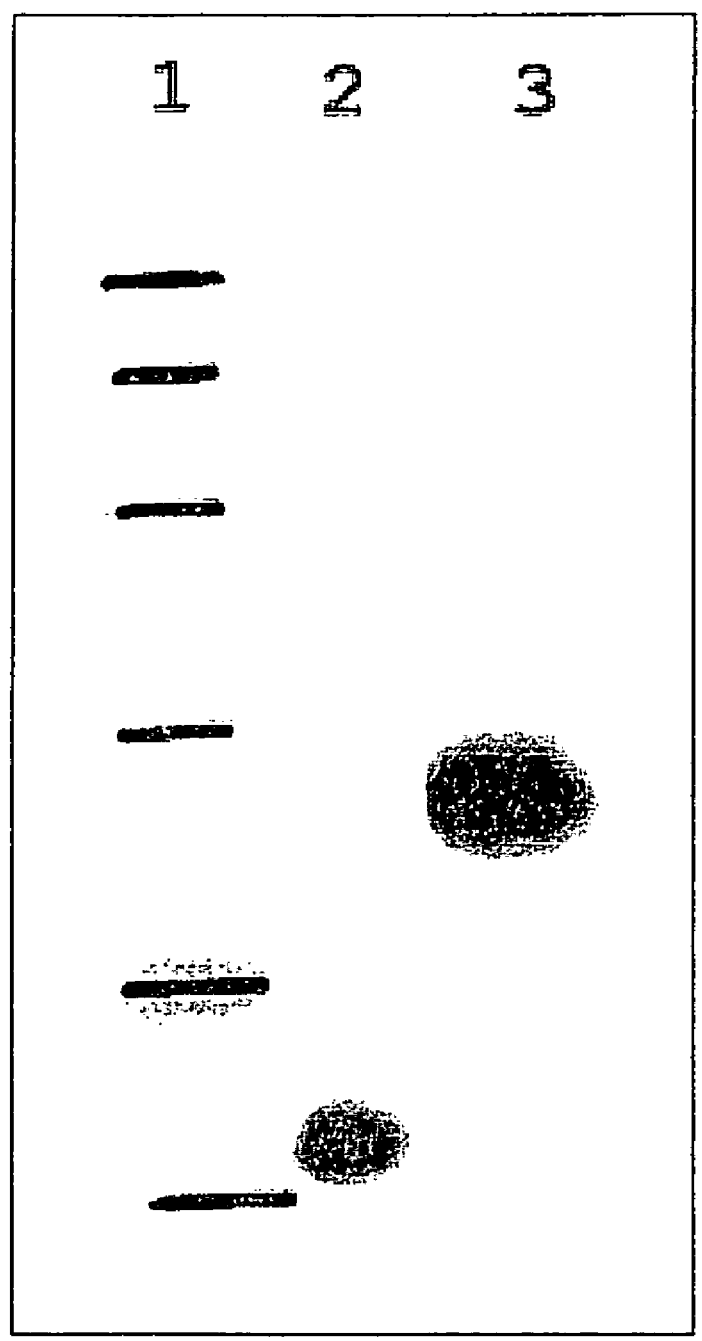
FIG. 1 shows the detection of monomeric (lane 2) and dimeric (lane 3) recombinant MP52 by polyclonal antibodies developed in chicken. Lane 1: Molecular Weight Marker (15,4/18,3/29,5,149,5/74,25/11 11,4/214,2 kD).

The following examples shall explain the invention more illustratively and are not considered to be restrictive.

Example 1

Preparation of Chicken Anti-human Polyclonal MP52 Antibodies

Immunization of chickens was performed by intramuscular injections of each 300 to 400 μg recombinant MP52 produced in *E. coli*. The chickens were boosted every two or three weeks with 150 to 300 μg antigen each for about one year. For the purpose of immunization, the antigen was solubilized in a Tris/Urea buffer prior to mixing it with the adjuvant for chicken (LES+STM, PANSystems #25-0401) according to the manufacturers instructions. Antibodies were isolated from egg yolk. Intact yolks were separated carefully from the white of egg, washed several times with a gentle stream of distilled water and were broken by a razor. The broken yolks from three to four consecutive eggs were pressed through a sieve, pooled and the antibodies were subsequently purified by PEG precipitation as essentially described by Thalley, B. S. & Carroll, S. B. (Biotechnology 8, 1990, 934-938). They were mixed with seven volumes of egg extraction buffer (10 mM Na phosphate, 0.1 M NaCl, pH 7.5) and PEG 6000 was slowly added on ice accompanied by gentle stirring to a final concentration of 3.5%. When the PEG was completely dissolved, the solution was centrifuged (9000×g, 10 min, 4° C.), the pellet discarded and the supernatant filtered through cheesecloth to remove the lipid layer. PEG was added to a final concentration of 12% and centrifuged as described above. The pellet, containing the antibodies, was redissolved in extraction buffer (2 times the original yolk volume) and PEG was added again to a final concentration of 12% as described above. After centrifugation the supernatant was discarded and the pellet centrifuged twice (2 min, 4° C., 300×g) in order to remove remaining traces of PEG. The antibody pellet was resuspended in PBS containing 0.02% $NaN_3$ (original yolk volume), filtered (Nalgene #155-045) and the protein concentration was determined by the method of Bradford (Coomassie Protein Assay Reagent, Pierce #23200).

In order to remove antibodies which showed affinity to *E. coli* proteins, *E. coli* strain BL21(DE3)LysS was grown, lysed by sonication and the isolated proteins were covalently coupled to AminoLink Columns (Immuno Pure, Aminolink Kit, Pierce #44890) according to the manufacturer instructions (BL21-column). Aliquots of PEG purified antibodies from eggs were loaded on this column and the flow through containing antibodies against MP52 was collected. To further purify the antibodies which gave the best respond to MP52, several antibodies from the maxima at about 200-240 days after immunization were taken. Antibodies can be specifically purified by adsorption to and elution from their antigen for which several methods are known (see for example Antibodies, A Laboratory Manual, Cold Spring Harbor Laboratory, 1988, chapter 8). In such a method pure antigen is bound to a solid support and only antigen-specific antibodies within the polyclonal pool are allowed to bind. Unspecific antibodies can be removed by several washing steps and the specific antibodies can be eluted. This method is useful to isolate specific antibodies from a mixed polyclonal pool or antibodies recognizing only parts of MP52 or dimeric MP52. We used the binding of the antigen to filter membranes. MP52 was exposed to pieces of Immobilon membranes (Millipore

IPVH 000 10) and the protein was covalently crosslinked by UV-light. After blocking the membranes in 0.2% Tween 20 they were incubated with the antibodies, which were already purified by PEG precipitation and the BL21-column, overnight. After extensive washing steps, the antibodies were eluted with 0.1 M Glycine pH 2.8 and neutralized with Tris pH 9.

Example 2

Confirmation of Antibody Specificity by Western Blotting

A polyacrylamide gel (15% PAGE, 1.5 mm) was equilibrated for 5-10 min in transfer buffer (0.7 M Glycine, 0.026 M Tris, 15% ethanol, 10 mM DTT). A PVDF membrane (ImmobilonP-Transfermembran, Millipore #IPVH 00010) was cut to an equivalent size compared to the gel (about 8.5×5.5 cm separating gel), shortly soaked in methanol, rinsed with water and subsequently equilibrated in transfer buffer for 5-10 minutes. The transfer was performed in transfer buffer for 1 hour at 4° C. using a constant voltage (100 V) in an electrophoresis chamber from Hoefer (TE 22 Mini Transphor). Subsequently the membrane was washed three times (5 min each) in washing buffer (PBS, 0.1% Tween-20) by shaking at room temperature. For the subsequent treatments we used the reagents of the Western-Light™ Rabbit Kit from TROPIX/SERVA (WL10RC). The membrane was blocked in blocking buffer (0.2% I-Block, PBS, 0.1% Tween-20, 0.02% $NaN_3$, prepared according to the manufacturers instructions) for 1.5 hours at room temperature or alternatively over night at 4° C. The MP52 recognizing antibody was diluted 1:10000 in blocking buffer. The membrane was incubated for 1.5 hours at room temperature or over night at 4° C. with this first antibody. After washing for 3 times (10 min each) in blocking buffer, the Alkaline Phosphatase conjugated secondary antibody (SIGMA A9171) was diluted 1:10000 in blocking buffer and incubated with the membrane for 45-60 min at room temperature. The membrane was washed again 3 times (10 min each) in blocking buffer. For the purpose of detection the membrane was incubated two times (5 min each) in assay buffer (0.1 M Diethanolamine, 1 mM $MgCl_2$ pH 10.0), 5 min in Nitro-block (diluted 1:20 in assay buffer), again two times (5 min each) in assay buffer, 5 min in the substrate solution (substrate diluted 1:100 in assay buffer, about 3 ml for each membrane) and subsequently placed between two thin sheets of transparent foil. The exposure time to a high performance luminescence detection film (Hyperfilm ECL, Amersham #RPN 3103) was within the range of a few seconds to several minutes depending on the strength of the signal. The MP52 chicken antibodies were able to detect monomeric and dimeric MP52. FIG. 1 shows the positive detection of monomeric (lane 2) and dimeric (lane 3) MP52. Lane 1: Molecular Weight Marker (15,4/18,3/29,5,/49,5/74, 25/111,4/214,2 kD)

Example 3

Demonstration of Antibody Specifity in Tissue Cross Sections

Figure 2:
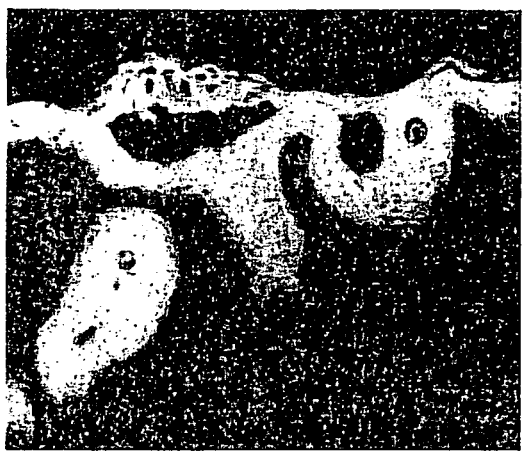
FIG. 2A-C shows cross sections with unabsorbed MP52 antibodies (2A) in comparison to the absorption of chicken anti-human polyclonal MP52 antibody by either 0.5 μg (2B) and 1 μg of monomeric MP52 (2C).
Figure 2:
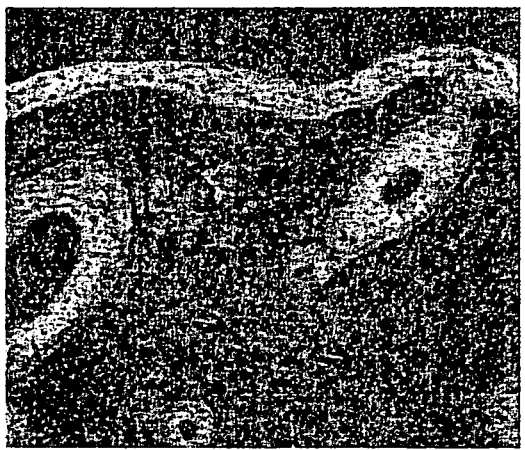
Figure 2:
Figure 3:
FIG. 3A-D shows positive immunostainings of different cross sections of human skin: epidermis (A1, C6), hair root sheath (A2), sebaceous glands (A3), sweat glands (B4, D7) and hair follicle (B5).
Figure 3:
Figure 3:
Figure 3:

To distinguish MP52-specific staining from unspecific stainings caused by the secondary antibody, cross sections of human skin were prepared as described under example 4. incubated with primary chicken anti-human polyclonal MP52 antibody and secondary FITC-coupled goat anti-chicken antibody To visualize background stainings produced by the secondary antibody, primary MP52 antibody was absorbed by addition of either 0.5 or 1 µg monomeric MP52 (2 hours, room temperature, moderate shaking), resulting in strong reduction of MP52 specific immunofluorescence The remaining weak colouring was caused by unspecific secondary antibody cross reactions with connective tissue components. FIG. 2A-C shows cross sections with unabsorbed MP52 antibodies (2A) in comparison to the absorption of chicken anti-human polyclonal MP52 antibody by either 0.5 µg (2B) and 1 µg of monomeric MP52 (2C).

Example 4

Preparation and Immunostaining of Different Skin Samples (Non Scalp)

Paraffin sections of human skin regions were analysed for MP52 expression by using a common sandwich immunostaining method. Immunohistochemistry is a basic technique and described in more detail in countless publications, e.g. by Johnstone A. and Thorpe R (Immunochemistry in Practice, 2nd edition 1987, Blackwell Scientific Publications, Oxford). After preincubation with BSE (1%) for 15 min and 100 mM DTT for 5 min, samples were treated with primary antibody (chicken anti-human polyclonal MP52 antibody, diluted 1:50) and incubated over night at 4° C. Subsequently unbound antibody was removed and the samples treated with secondary FITC-coupled goat anti-chicken antibodies for 1 hour at room temperature with Hoechst Bisbenzimid (2 ng/ml). Strong MP52 expression could be detected in several skin related cell structures, e.g. epidermis, hair rooth sheath and hair follicle as well as in different types of glands.

FIG. 3A-D shows positive immunostainings of different cross sections of human skin: epidermis (A1, C6), hair root sheath (A2), sebaceous glands (A3), sweat glands (B4, D7) and hair follicle (B5).

Example 5

Preparation of Mouse Anti-human Monoclonal MP52 Antibodies

Monoclonal antibodies directed against MP52 were isolated according to conventional methods. A complete description of the preparation and characterization of the above mentioned anti-human monoclonal MP52 antibodies can be found in EP 0 919 617. General techniques of monoclonal antibody production are further described in detail by Peters, J. H. & Baumgarten, H. (1990, Monoklonale Antikörper—Herstellung und Charakterisierung, Springer Verlag, 2. Auflage) and by Harlow, E. and Lane, D. (Antibodies, A Laboratory Manual, Cold Spring Harbor Laboratory, 1988, chapter 6).

Example 6

Detection of MP52 in Human Scalp

Figure 4:
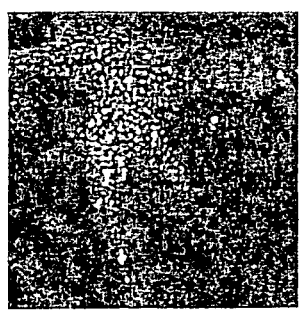
FIG. 4A-F shows positive (red) immunostainings of different cross sections of human skin: epidermis (A), blood vessels (B), neurons (C,D), upper portion of the hair follicle/infundibulum (E,F).
FIG. 4G: negative control (blue counterstain).
Figure 4:
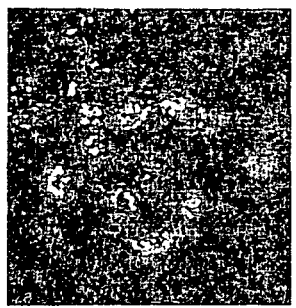
Figure 4:
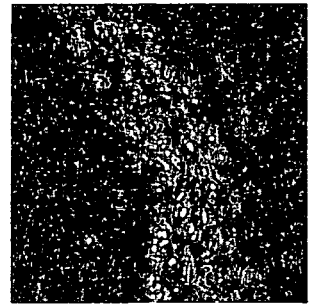
Figure 4:
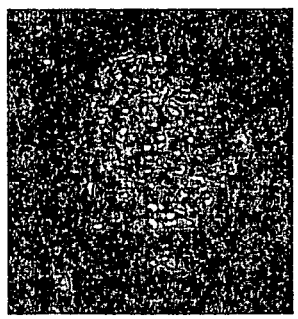
Figure 4:
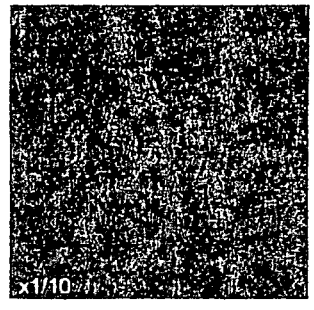
Figure 4:
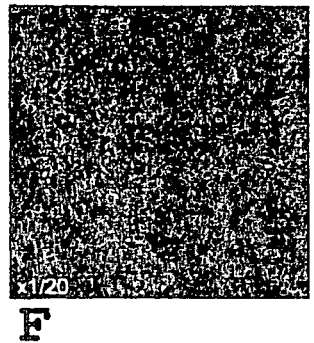
Figure 4:
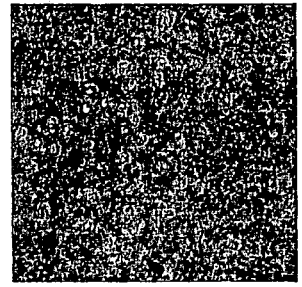

Mouse anti-human monoclonal MP52 antibodies (example 4) were used to detect MP52 in cryosections of human scalp. Cryosections were blocked for 15 min with 5% skimmed milk/0.02% Triton. MP52 Antibodies were diluted 1:75 and subsequently applied for 30 min at room temperature. After this period slides were washed (2×10 min) with PBS (phosphate buffered saline) buffer, followed by 30 min incubation with secondary antibodies (CY3 anti-mouse (red fluorescence), diluted 1:5000). Samples were shortly dipped in aqua dest., soaked in pure ethanol for 5 min and finally air dried. MP52 expression could be detected in several epidermal cell types, hair follicle, neurons and blood vessels FIG. 4A-F shows positive (red) immunostainings of different cross sections of human skin: epidermis (A), blood vessels (B), neurons (C,D), upper portion of the hair follicle/infundibulum (E,F). FIG. 4G: negative control (blue counterstain).

Example 7

Effect of MP52 on Epithelial Growth

Figure 5:
FIG. 5 shows cross sections of 8 days old organotrophic cell cultures, grown either with 100 ng/ml (inactive) nonrefolded monomeric MP52 (A, negative control) or 100 ng/ml (active) dimeric MP52 (B).
Figure 5:
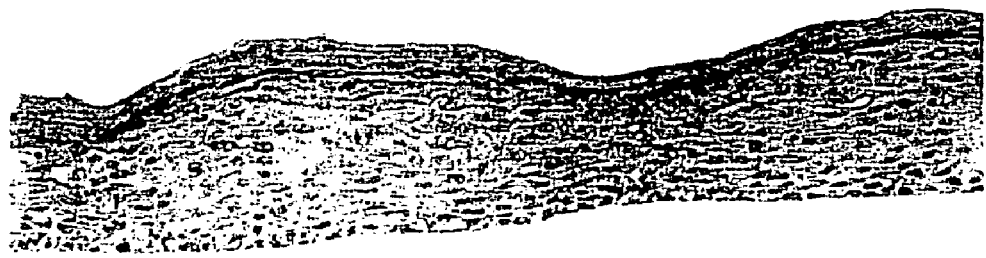

In order to demonstrate the positive growth promoting effect of MP52 on skin related tissue, epithelial formation/proliferation was studied in vitro via an organotrophic cultivation of human keratinocytes and fibroblasts, simulating an epidermis like structure. Human fibroblasts were embedded in a collagen type 1 gel matrix (3.2 mg/ml). Additionally, keratinocytes were grown on top of the gel matrix. In vitro cultivation of these cells was performed during a period of 9 days with bidaily replacement of FCS-free cell culture medium. To identify possible growth promoting effects, 100 ng/ml (active) dimeric MP52 was added to the medium. Instead of (active) dimeric MP52, 100 ng/ml (inactive) non-refolded monomeric MP52 was added to the culture medium of samples which served as negative controls. Epithelial cultures grown with addition of dimeric MP52 consisted of significantly more cell layers than negative control cultures. Furthermore, addition of MP52 neutralizing antibodies to organotrophic cell cultures resulted in inhibition of epithelial growth. FIG. 5 shows cross sections of 8 days old organotrophic cell cultures, grown either with 100 ng/ml (inactive) nonrefolded monomeric MP52 (A, negative control) or 100 ng/ml (active) dimeric MP52 (B).

The invention claimed is:

1. A method for improving wound healing and/or wound repair of skin tissue in a mammal, comprising administering an amount of a cytokine effective to improve wound healing and/or wound repair of skin tissue, wherein said cytokine is selected from the group consisting of GDF-5 or a part thereof wherein said part includes the 7 cysteine region and said GDF-5 or part thereof is modified by changing a cysteine required for dimer formation to another amino acid resulting in a monomeric cytokine and retains the wound healing and/or wound repair activity of the mature protein, to a mammal in need of wound healing or wound repair of skin tissue such that wound healing and/or wound repair of skin tissue is improved.

2. The method according to claim 1, wherein the amount of said cytokine administered is effective to stimulate recruitment of inflammatory cells.

3. The method according to claim 1, wherein the amount of said cytokine administered is effective to stimulate reepithelization.

4. The method according to claim 1, wherein the amount of said cytokine administered is effective to stimulate collagen synthesis and deposition.

5. The method according to claim 1, wherein the amount of said cytokine administered is effective to stimulate fibroblast proliferation.

6. The method according to claim 1, wherein the amount of said cytokine administered is effective to stimulate neovascularization.

7. The method according to claim 1, further comprising administering at least one further cytokine of the TGF-β superfamily to said mammal in combination with said modified GDF-5 or part thereof wherein said part includes the 7 cysteine region.

8. The method according to claim 1, further comprising administering NGF, neurotrophin, EGF, EGF-like proteins, VEGF, TGF-a, CNTF, BDNF, FGF, IGF, or KGF to said mammal in combination with said GDF-5 or part thereof including at least the 7 cysteine region.

9. The method according to claim 1, wherein said mammal is a human.

* * * * *